United States Patent [19]

Belgorod

[11] Patent Number: 4,724,522
[45] Date of Patent: Feb. 9, 1988

[54] METHOD AND APPARATUS FOR MODIFICATION OF CORNEAL REFRACTIVE PROPERTIES

[76] Inventor: Barry M. Belgorod, 200 E. 72nd St., Suite 16H, New York, N.Y. 10021

[21] Appl. No.: 867,313

[22] Filed: May 27, 1986

[51] Int. Cl.[4] .................. A61B 17/00; A61N 5/00; G06F 15/42

[52] U.S. Cl. .................. 364/415; 128/303.1; 219/121 LQ

[58] Field of Search .......... 128/303.1; 364/415, 364/464–465; 219/121 LQ, 121 LS, 121 LT, 121 LG, 121 LN, 121 LH, 121 LA

[56] References Cited

U.S. PATENT DOCUMENTS

| | | | |
|---|---|---|---|
| 3,621,181 | 11/1971 | Young | 219/121 LU |
| 3,769,963 | 11/1973 | Goldman et al. | 128/303.1 |
| 3,965,327 | 6/1976 | Ehlscheid | 219/121 LP |
| 3,982,541 | 9/1976 | L'Esperance | 128/303.1 |
| 4,044,936 | 8/1977 | Obersby | 219/121 LU |
| 4,164,222 | 8/1979 | Prokhornv et al. | 128/303.1 |
| 4,170,726 | 10/1979 | Okuda | 219/121 LM |
| 4,173,980 | 11/1979 | Curtin | 128/303 R |
| 4,215,694 | 8/1980 | Isakov et al. | 128/303.1 |
| 4,266,548 | 5/1981 | Davi | 128/303.1 |
| 4,309,998 | 1/1982 | Aron nee Rosa et al. | 128/303.1 |
| 4,336,809 | 6/1982 | Clark | 128/303.1 |
| 4,427,872 | 1/1984 | Saunders | 219/121 LH |
| 4,461,294 | 7/1984 | Baron | 128/303.1 |
| 4,469,931 | 9/1984 | Macken | 219/121 LG |
| 4,533,812 | 8/1985 | Lorenz | 219/121 LH |
| 4,551,608 | 11/1985 | Opower | 219/121 LQ |
| 4,563,565 | 1/1986 | Kampfer | 219/121 LJ |
| 4,665,913 | 5/1987 | L'Esperance, Jr. | 128/303.1 |

FOREIGN PATENT DOCUMENTS

| | | |
|---|---|---|
| 0083494 | 7/1983 | European Pat. Off. |
| 0111060 | 6/1984 | European Pat. Off. |
| 0151869 | 11/1984 | European Pat. Off. |
| 1040181 | 10/1954 | Fed. Rep. of Germany ...... 128/395 |
| 1288245 | 1/1969 | Fed. Rep. of Germany . |
| 3148748 | 7/1983 | Fed. Rep. of Germany ... 128/303.1 |

OTHER PUBLICATIONS

Laser & Elektrooptik, vol. 10, No. 1, Mar. 1978, "The Laser Micro Beam as a Tool for Tissue Sampling in Biochemistry".

Advanced Techniques in Opthalmic Microsurgery", by L. Girard, publ. 1981, pp. 84, 107–110, 114, 116, 123, 125–133 and 143–171.

"Thermokeratoplasty (TKP) Temperature Profile", by E. Shaw et al., Investigative Opthal., Mar. 1974, pp. 181–186.

"A Technique for the Selective Heating of Corneal Stroma", by Doss et al., Contact and Intraocular Lens Med. Jour., vol. 6, No. 1, 1980, pp. 13–17.

"Extreme Sensitivity in the Corneal Epithelium to Far UV ArF Excimer Laser Pulse" by J. Taboda et al., Aerospace Medical Assoc., 1981 Meeting, San Antonio, TX.

(List continued on next page.)

Primary Examiner—Jerry Smith
Assistant Examiner—Gail O. Hayes
Attorney, Agent, or Firm—Morgan & Finnegan

[57] ABSTRACT

A method and apparatus for modifying corneal refractive properties includes a laser source, computer control, and a plurality of deflectors including at least one rotating and translating deflector. A beam emitted from the laser source is deflected by the rotating and translating deflector in a controlled manner such that the beam strikes the cornea tangentially, ablating or lathing the contacted surface. The apparatus is computer controlled to intra-operatively determine the visual axis, monitor fixation, monitor changing refractive error, adjust the rotating and translating deflector and activate and deactivate the laser. The invention allows the radius of curvature of the cornea to be modified in vivo or in vitro. The cornea is lathed tangentially in either a natural or frozen state in an area centered about its optical axis, encompassing its optical zone. In one embodiment, a rotating arm, rotating in a plane perpendicular to the optical axis of the cornea, transmits the laser beam to the variable deflector.

50 Claims, 16 Drawing Figures

OTHER PUBLICATIONS

"Opthalmic Lasers: Photocoagulation, Photoradiation and Surgery", L'Esperance, Jr., (1983); The C. V. Mosby Company, pp. 8-27.

J. Taboada et al., "Response of the Corneal Epithelium To KrF Excimer Laser Pulses", Health Physics, vol. 40, pp. 677-683, 1981.

S. L. Trokel, M.D., et al., "Excimer Laser Surgery of the Cornea", American Journal of Ophthalmology, vol. 96, pp. 710-715, 1983.

A. M. Cotliar, M.D., et al., "Excimer Laser Radial Keratotomy", Ophthalmology, vol. 92, pp. 206-208, 1985.

Carmen A. Puliafito, M.D., et al., "Excimer Laser Ablation of the Corneal and Lens", Ophthalmology, vol. 92, pp. 741-748, 1985.

John Marshall, PhD., et al., "An Ultrastructural Study of Corneal Incisions Induced by an Excimer Laser at 193 nm", Ophthalmology, vol. 92, pp. 749-758, 1985.

REFRACTIVE ERRORS

FIG. 1

EMMETROPIA

FIG. 2

MYOPIA

FIG. 3

HYPEROPIA

RCI = INITIAL CORNEAL RADIUS OF CURVATURE
RCF = FINAL CORNEAL RADIUS OF CURVATURE
TI = INITIAL CORNEAL THICKNESS
TF = FINAL CORNEAL THICKNESS

METHOD AND APPARATUS FOR MODIFICATION OF CORNEAL REFRACTIVE PROPERTIES

BACKGROUND OF THE INVENTION

The invention pertains to a method and apparatus for modifying the refractive properties of the eye. More particularly, the invention pertains to a method and apparatus for correcting refractive errors by modifying the cornea of the eye.

The human eye functions by sensing light rays. Such light rays tend to be focused as they pass through the cornea, the aqueous humor, the lens and the vitreous humor. Ideally, the focal point of light, after passing through these components, will be at the retina. Emmetropia, or the lack of refractive error, is thus characterized by the focal point of the light entering the eye from an infinite distance and falling on the retina.

Figure 1:
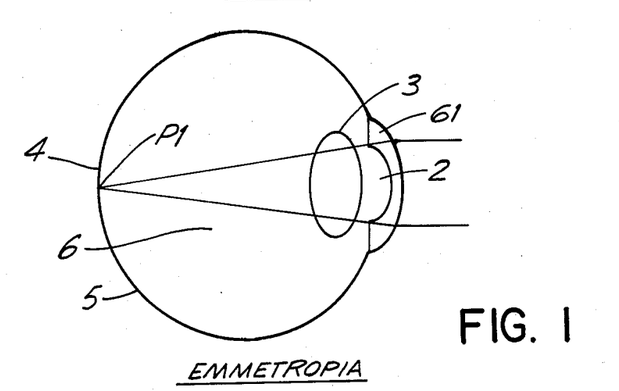
FIGS. 1-3 are schematic illustrations of human eyes illustrating the conditions of emmetropia, myopia and hyperopia, respectively.

FIG. 1 illustrates the condition of emmetropia. As shown in FIG. 1, light enters the eye through the cornea 61 and passes through the cornea, the aqueous humor 2, the crystalline lens 3 and the vitreous humor 6. The light is focused by the refractive power of the cornea 61, the aqueous humor 2, the crystalline lens 3 and the vitreous humor 6 to a focal point P1 which, in the case of emmetropia as shown in FIG. 1, is at the retina 4. The globe of the eye is generally indicated at numeral 5 in FIG. 1.

Figure 2:
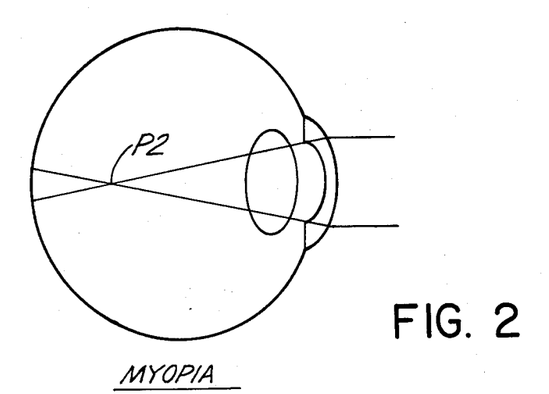
Figure 2:
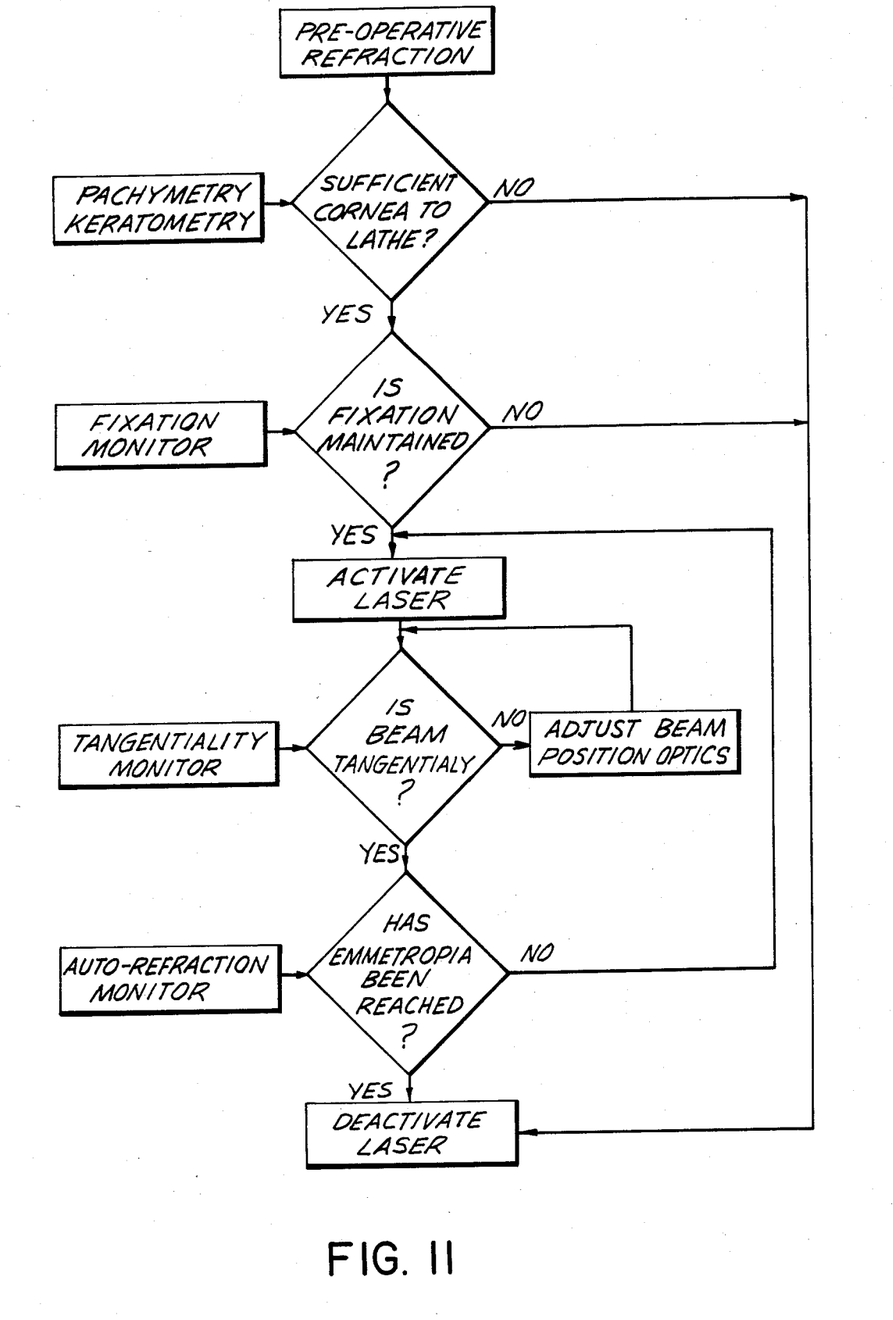
Figure 3:
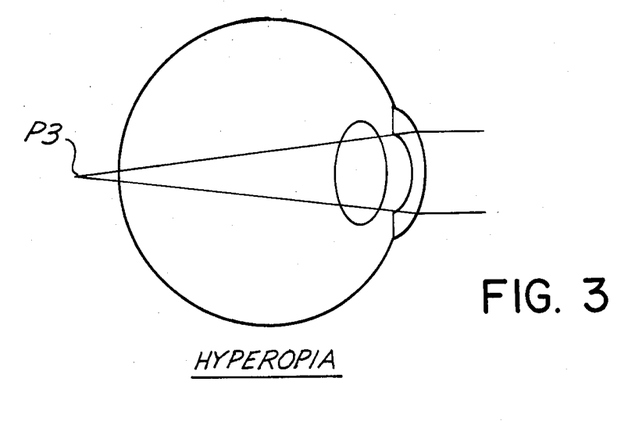

Billions of human beings suffer impaired vision due to refractive errors of the eye characterized by the focal point of light failing to be at the retina, but rather falling short of or behind the retina. Common refractive errors of the eye fall into three main categories: myopia, hyperopia, and astigmatism. Myopia (FIG. 2), also known as nearsightedness, results when the focal point P2 of the eye is located anterior to the retina 4. Hyperopia (FIG. 3), also known as farsightedness, results when the focal point of the eye is located posterior to the retina 4. Astigmatism results when the eye has different refractive errors at different meridians. Thus, astigmatism may be present as a combination of any two of emmetropia, myopia and hyperopia in the same eye. For example, in an astigmatic eye, light entering the eye in a horizontal meridian may be focused anterior to the retina, while light entering the eye in a vertical meridian may be focused posterior to the retina.

As is well known, the cornea provides approximately two-thirds ($\frac{2}{3}$) of the refractive power of the eye. This is primarily due to the optically powerful air/cornea interface created by the large disparity of refractive indices between the air (1.00) and the cornea (approximately 1.37). The aqueous/lens interface causes further refraction within the eye.

Because the cornea is such an important factor in refraction of the eye, a wide variety of methods and apparatuses have been applied in the past to alter the cornea in an effort to eliminate refractive errors. For example, contact lenses, which are also commonly used as refractive entities in themselves, have been intentionally malfitted to temporarily alter the corneal curvature. The later technique is known as "orthokeratology" and generally results in only a temporary change in the corneal curvature. Orthokeratology has a further deficiency in that it is known to induce potentially serious corneal inflammation and scarring.

Several other techniques are known for altering the cornea in various ways to compensate for refractive errors of the eye. For example, radial keratotomy involves the making of radially orientated slit-like incisions in the cornea, in various patterns, to attempt to correct myopia and/or astigmatism. At present, however, the results of radial keratotomy are unpredictable and are often not reproducible in the same patient. Additionally, it is as yet unclear how long the results of radial keratotomy last. Further, there have been reports of corneal degenerations, injections and distortions after radial keratotomy, such conditions obviously having the potential for serious visual loss.

It is also known to use lasers for altering the condition of the cornea. U.S. Pat. 4,461,294 illustrates the use of the thermal effect of a laser to induce corneal-recurving scars by imbedding, under pressure, light absorbing colored bodies in the cornea in a radial pattern. The colored bodies in the cornea are exposed to a thermal laser through a matched, slitted diaphram. In the technique disclosed by the U.S. Pat. No. 4,461,294 patent, corneal tissue is burned for the purpose of creating scar tissue.

Another technique for modifying the cornea, known as lamellar keratoplasty involves the taking of a slice of a patient's cornea, or a donor's cornea, freezing the portion and lathing it in a hard-frozen state to a new curvature prior to suturing onto the eye of the patient. Particular methods employing this technique include keratomileusis, keratophakia, and epikeratophakia, each of which requires cutting and suturing of the patient's cornea.

Yet another cornea modification technique is disclosed in European Patent Application No. 0 151 869 which discusses a device for exposing the cornea to an excimer laser in perpendicular fashion to reshape the cornea. The European application discloses a laser which is directed at the eye substantially along the visual axis of the eye. Removal of tissue is effected by exposing the cornea head-on to varying flux densities and exposure times in either rectilinear or spiralling fashion. This head-on exposure to the radiation of the laser would presumably expose the eyes delicate internal structures, such as the iris, the lens and the retina, to potentially damaging levels of radiation. Additionally, in such a device, if the output of the laser were inadvertently increased, deeper levels of tissue penetration could result in accidental preforation of the cornea or irregular corneal refracting surfaces.

To date, there are no known non-invasive devices or methods which provide effective, safe, predictable and reproducible modifications of corneal curvature for effectively compensating for the refractive errors of the eye.

It is therefore an object of the invention to provide a method and apparatus for accurately shaping the cornea to compensate for refractive errors of the eye.

It is a further object of the invention to provide a method and apparatus for reshaping the cornea of the eye in vivo without the need for removing and then suturing the corneal tissue.

It is a further object of the invention to provide a method and apparatus for shaping the cornea of the eye in which there is no necessity for freezing the corneal tissue prior to shaping but which may be used in conjunction with freezing techniques.

It is a still further object of the invention to provide a method and apparatus for shaping the cornea which reduces or eliminates the risk of accidental damage to the cornea and the other components of the eye, such as the iris, the lens and the retina.

It is a still further object of the invention to provide a method and apparatus which meets the foregoing objectives and which is safe, predictable, and reproducible.

SUMMARY OF THE INVENTION

These and other objects of the invention are met by providing a method and apparatus for reshaping the cornea of the eye, including a laser source, computer control, and a rotating and translating deflective member such as a mirror. The rotating and translating deflective member is guided by the computer to direct a laser beam emitted from the laser source to tangentially strike the cornea of the eye, causing controlled corneal ablation and thereby modifying the radius of curvature of the cornea. With the invention, the cornea is lathed tangentially in either its natural or frozen state, in vivo or in vitro, in an area centered about its optical axis and encompassing its optical zone by either a non-thermal emission such as an ultraviolet or excimer laser, or a thermal emission such as an infra-red laser, under automated or manual control.

The invention is effective to modify the corneal curvature and thereby its refractive properties by shaving or vaporizing part of the optical zone of the cornea in a precisely calibrated and predictable manner, eliminating the need for cutting blades or mechanical lathing which were heretofore provided. The invention also obviates the need for suturing and scarring of the cornea. In addition, since the incident laser beam in the invention strikes the cornea only tangentially, changes in the frequency or power output of the laser would not carry the risk of perforation, and delicate intraoccular structures would not be directly exposed to the laser.

BRIEF DESCRIPTION OF THE DRAWINGS

The invention will be described in greater detail below by way of reference to the following drawings, in which:

FIG. 11 is an operational flow chart describing the functioning of an apparatus according to the invention;

DETAILED DESCRIPTION OF THE DRAWINGS

Figure 4:
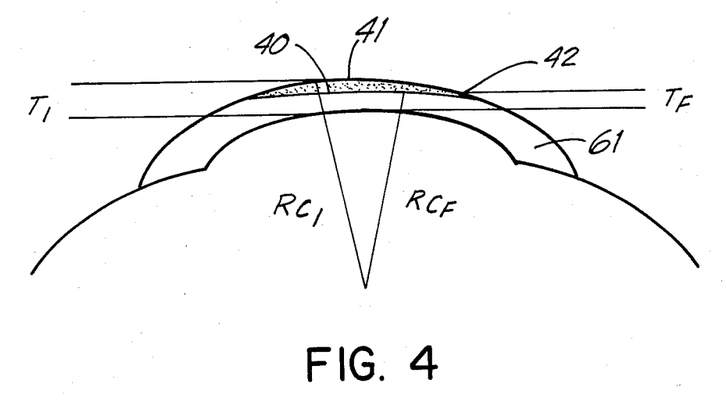
FIG. 4 illustrates the ablation of corneal tissue in the treatment of a myopic patient.
Figure 5:
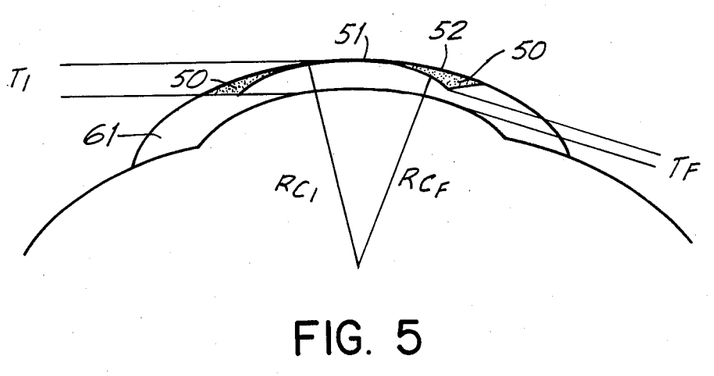
FIG. 5 illustrates the ablation of corneal tissue in the treatment of a hyperopia patient.

Surgical procedures for modifying corneal refractive properties in treating the conditions of myopia and hyperopia with an apparatus according to the invention are described by way of reference to FIGS. 4 and 5. FIGS. 4 and 5 illustrate schematic cross-sectional views of the eye of a myopic patient (FIG. 4) and a hyperopic patient (FIG. 5). In both FIGS. 4 and 5, $RC_I$ depicts the initial or pre-operative corneal radius of curvature, $RC_F$ depicts the final or post-operative corneal radius of curvature, $T_I$ depicts the initial or pre-operative corneal thickness and $T_F$ depicts the final or post-operative corneal thickness.

FIG. 4 illustrates the treatment of myopia with an apparatus according to the invention. For treatment of the myopic patient, corneal tissue 40 may be removed from the apex 41 outward to the periphery 42, altering the cornea from its initial corneal thickness $T_I$ and initial corneal radius of curvature $RC_I$ to a lessened final corneal thickness $T_F$ and a lessened final corneal radius of curvature $RC_F$. Treating myopia (FIG. 4) in accordance with the invention should thus result in a flatter cornea.

In correcting or treating hyperopia (FIG. 5), the resultant corneal radius of the curvature should be smaller, resulting in a steeper cornea. Thus, in treating the hyperopic patient, the corneal radius of curvature and corneal thickness are both reduced as corneal tissue 50 is removed primarily from the mid-pheriphery 52 as illustrated in FIG. 5.

The treatment methods of FIGS. 4-5 have been practiced in the past using, for example, lamellar keratoplasty techniques.

Figure 6:
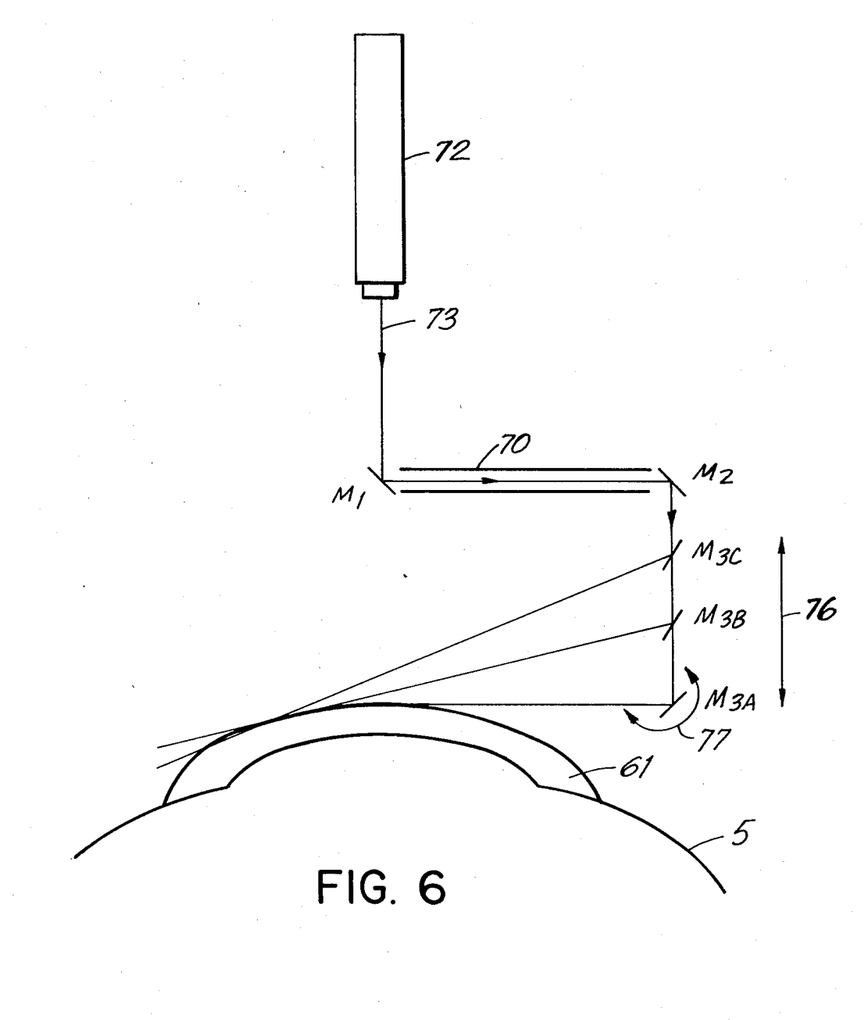
FIG. 6 is a schematical plan view of an apparatus according to the invention positioned about a human eye.
Figure 7:
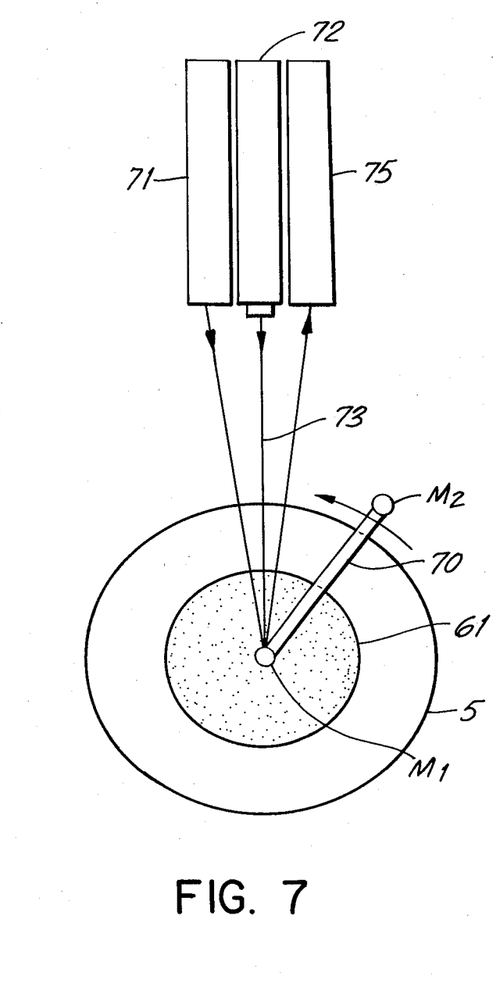
FIG. 7 is a partial elevational view of one embodiment of the invention positioned about a human eye illustrating a rotating arm for transmitting a laser beam to a deflector.

FIG. 6 is a partial planar cross-sectional view and FIG. 7 is a partial elevational view of a laser delivery device according to the invention provided about a human eye 5 including cornea 61. Shown in FIG. 6 are a laser source 72, a rotating arm 70 and three mirrors: an incident mirror $M_1$, and intermediate mirror $M_2$ and a variable mirror $M_3$. The laser source 72 and the incident mirror $M_1$ are positioned on the optical axis of the cornea. FIG. 7 also illustrates an autorefraction system including an autorefractor emitter 71 and an autorefractor detector 75.

In the embodiments of FIGS. 6 and 7, incident mirror $M_1$ and intermediate mirror $M_2$ are mounted on rotating arm 70 at fixed angles such that a laser beam 73 generated by laser source 72 is deflected off mirror $M_1$ along rotating arm 70 to intermediate mirror $M_2$ in a plane perpendicular to the optical axis. Intermediate mirror $M_2$ is positioned to deflect the laser beam 73 to the variable aiming mirror $M_3$, which is shown in three example positions $M_{3A}$, $M_{3B}$ and $M_{3C}$ in FIG. 6.

Aiming mirror $M_3$ may be bearing-mounted within a parallel-bar slide 74 suspended from arm 70, for translation in the direction of the double-headed arrow 76 and may be pivotally mounted within the slide 74 for rotation in the direction of the double-headed arrow 77 of FIG. 6. Both rotation and translation of variable mirror $M_3$ may be achieved by the action of lightweight stepping or pulse motors (not shown) under the control of the system computer (see FIG. 9). Variable mirror $M_3$, (FIG. 6) which receives the laser beam from intermediate mirror $M_2$, may thus be adjusted under the direction of the computer controller 90 to deflect and thereby aim the laser beam to effect tangential lathing of the corne in accordance with the invention.

Referring to FIG. 7, the rotating arm 70, which may be hollow or comprised of fiber optic or other transmitting elements, transmits the deflected laser beam from the incident mirror $M_1$ to the intermediate mirror $M_2$. In accordance with this embodiment of the invention, arm 70 rotates in the direction of the arrow to provide prescribed tangential lathing symmetrically about the entire circumference of the cornea 61. Slide 74 (FIG. 6) may be fixed or otherwise secured to aim 70 so as to join in the rotating movement of the arm 70 about the optical axis of the cornea 61. Thus, as the arm 70 rotates, carrying with it incident mirror $M_1$, intermediate mirror $M_2$, slide 74 and aiming mirror $M_3$, a properly aimed laser beam (aimed by rotating and/or translating mirror $M_3$) will lathe the cornea trically in accordance with prescribed surgical procedure.

In the general, the pattern of tangential lathing may be a microscopically-fine spiral pattern having components from both the rotation of arm 70 and the translation of mirror $M_3$.

Figure 10:
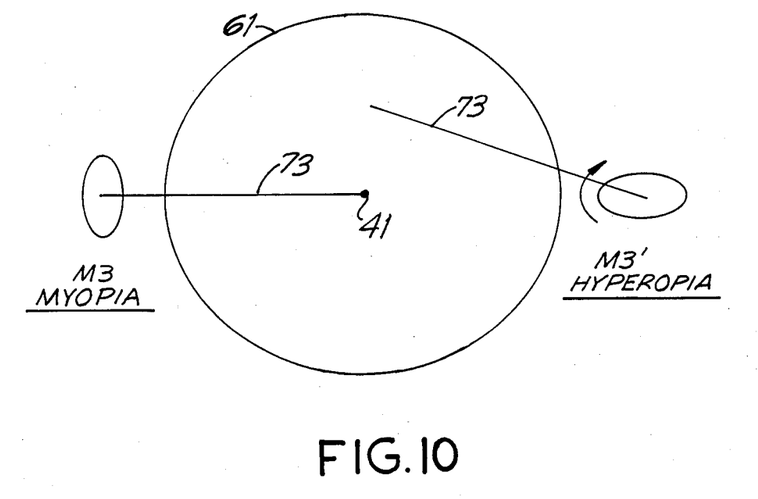
FIG. 10 illustrates the alignment of directing elements to correct myopia and hyperopia in an apparatus according to the invention.

As FIG. 4 illustrates, treatment of the myopic patient requires ablation of the apex 41 tapering outward to the pheriphery 42, the tissue to be ablated being designated by numeral 40. Referring to FIG. 6, to effect such ablation for the myopic case, variable element $M_3$ must be capable of rotation along one axis as well as translation in the direction of the arrow 76. FIG. 10 thus illustrates, for treatment of myopia, that the variable element $M_3$ should be aligned with the visual axis. The ablation pattern will thus be centered about the visual axis.

Treatment of hyperopia, on the other hand, requires ablation of primarily the mid-periphery 52 as shown in FIG. 5, with the corneal tissue to be ablated being indicated by numeral 50. To achieve such ablation, the variable element $M_3$ of FIG. 6 must be capable of rotation along two, perpendicular axes as well as translation. Thus, FIG. 10 illustrates that for the treatment of hyperopia, element $M_3'$ will be directed off of the visual axis and thus should be capable of rotation about an additional axis. In this case, the tissue will be primarily from an area away from the optical center of the cornea.

The invention, in preferred embodiments, may include a variety of safety features in addition to interactive monitors under computer control. As the corneal thickness will be altered in the treatments illustrated in FIGS. 4 and 5, it is important to determine pre-operatively how thick the cornea will be post-operatively, so as not to perforate the cornea while attempting to change its curvature. For this reason, referring to FIG. 9, pre-operative data of keratometry 91 (i.e. the corneal curvature) and pachymetry 92 (i.e. corneal thickness, "normal" being approximately 0.5 mm thickness at the corneal apex) are inputted into a system command computer 90. Data of refraction 93 (e.g. expressed in diopters) may also determined pre-operatively and provided to the system computer controller. An autorefractor emitter 71 and director 73 (FIG. 7) may be provided to interactively obtain refractive error conditions. The computer is programmed to calculate whether the amount to be lathed off of the cornea to achieve the desired refractive correction exceeds the amount that would alter the structural integrity of, or perforate, the cornea. If the amount to be lathed exceeds a programmed safe amount, the computer 90 will not allow the system to commence laser operation 94. If the calculations prove lathing to be a viable option, laser operation 94 will be activated. Durng laser operation, the computer 90 will monitor, in real time, the current refractive error 95, the visual axis 97, and the fixation 96 of the eye.

As FIGS. 6 and 7 illustrate, the laser beam 73 is incident on mirror $M_1$, perpendicular to the corneal apex and exactly on the visual axis. In preferred embodiments of the invention, the visual axis of the patient will be determined automatically using a visual fixation device testing for either centration of corneal light reflexes or for the "red reflex" response to a collimated light beam entering the pupil and reflecting off the retina and exiting the pupil. In preferred embodiments, fixation will be closely monitored during the lathing procedure (see FIG. 9, item 96), such that if fixation along the visual axis is lost, the laser will automatically cease operation.

As discussed above, aiming or variable mirror $M_3$ is capable of both rotation and translation, these movements preferably being controlled by calculations of the system control computer 90 based on both pre-operative and real time data. More particularly, the translation and rotation of element $M_3$ enable adjustment to the path of the laser beam such that the laser beam can be directed to vaporize, ablate, burn or slice microscopic, tangential sections of the cornea 61 from the apex to the periphery on-axis in the myopic case, (See FIGS. 4 and 10) and primarily from the mid-periphery off-axis in the hyperopia case (see FIGS. 5 and 10). In preferred embodiments, these procedures are done under constant guidance of the computer controller 90 and an autorefractor including an autorefractor emitter 71 and an autorefractor dectector 75 (FIG. 7) to insure that the refractive end-point (presumably emmetropia, FIG. 1) is not passed.

The system autorefractor may be provided along the visual axis to intra-operatively monitor the refractive properties of the eye and to provide real-time data to the computer as to the changing refractive power of the cornea. The computer may be programmed to interpret this data and, based on the data, to make appropriate adjustments to mirror $M_3$ or to terminate the procedure.

Figure 12:
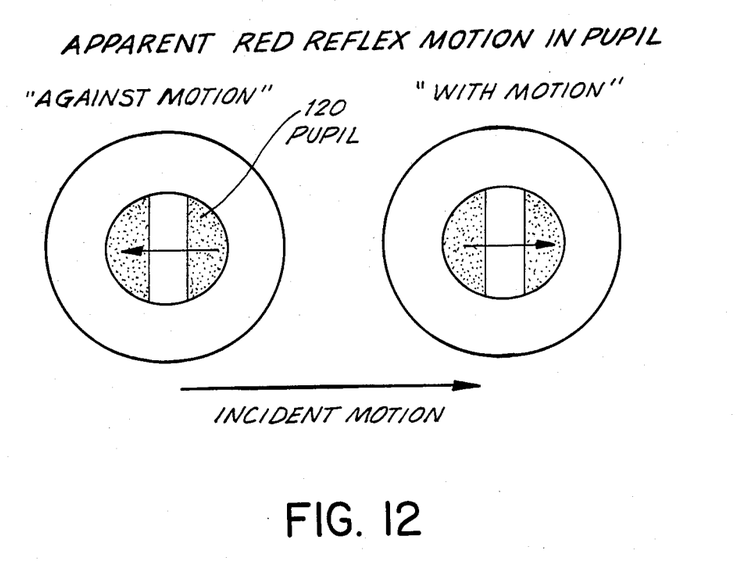
FIG. 12 illustrates the "red reflex" motion technique used in monitoring eye fixation in one apparatus according to the invention.

In one embodiment, the system autorefractor may comprise a rotating "chopper" disc to break-up a continuous light beam into moving pulse trains. Alternatively, a phased array of light emitting sources may be provided to accomplish the same effect. The moving pulse train, projected through an appropriate lens though the pupil, would generate apparent "against motion", "with motion" or "no motion" with respect to the directionality of the pulse train to signify to the system computer 90 that more myopic, more hyperopia or no additional corneal curvature correction would be indicated to achieve emmetropia. FIG. 12 illustrates apparent red reflex motion in a pupil 120, indicating "against motion" and "with motion" with respect to the incident motion of the pulse train. Such autorefraction mechanisms are, of course, well-known.

Figure 8:
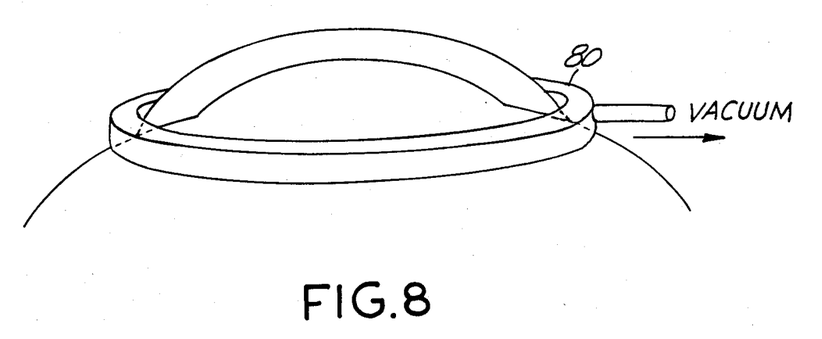
FIG. 8 illustrates a method of fixing the eye in position prior to and during an operation according to the invention.

Throughout the procedure according to the invention, the globe 5 (see FIG. 7) of the eye should be precisely fixated. This may be accomplished by use of a known vacuum fixation ring 80 (FIG. 8) which may be attached to an X-Y axis movement device to automatically adjust the axis of fixation of the eye. An electronic output of such an X-Y axis movement device will preferably signal the control computer 90 (FIG. 9) to deactivate the laser 72 upon detection of loss of fixation and should signal the computer when fixation has been re-established so that the lathing procedure can recommence.

Although the embodiment of FIGS. 6 and 7 discloses fixed angle mirrors $M_1$ and $M_2$, mirrors $M_1$ and $M_2$ can be easily replaced by a wide variety of non-mirror elements such as prisms, lenses, fiber-optic elements or holographic elements. Likewise, variable element $M_3$, disclosed in FIGS. 6 and 7 as a mirror, can be replaced with a prism, a lens, a fiber optic element or a holographic element. Additionally, it is contemplated that the invention may be embodied in apparatuses where the angles of the incident and intermediate elements $M_1$, $M_2$ are not fixed as shown in FIGS. 6 and 7 but rather may be variable and provided in a wide variety of geometries. Similarly, the arm 70 and slide 76 may be replaced by a variety of components provided the same enable a laser beam to be directed tangentially at the cornea about the entire circumference thereof.

Figure 14:
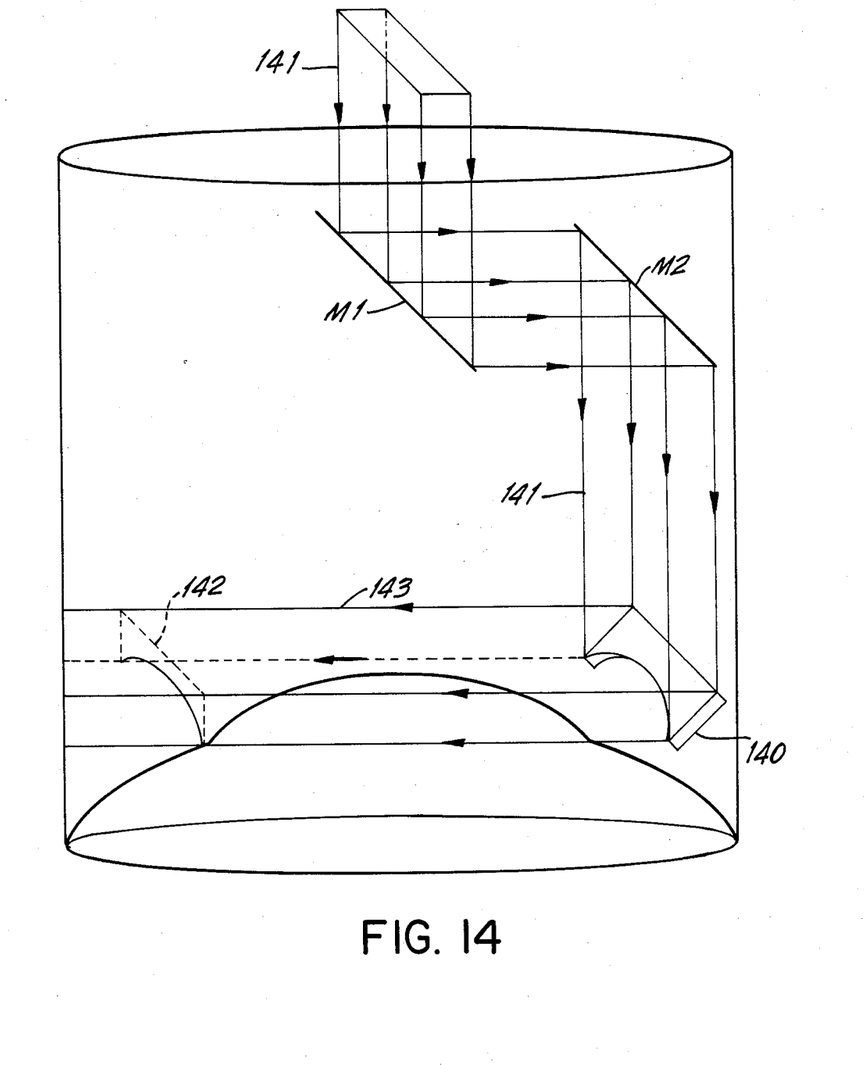
FIG. 14 is a partial perspective view of a curved deflector element according to one embodiment of the invention.

FIG. 14 illustrates a further embodiment of the invention wherein a curved optical element 140, such as a planar mirror with a curved inferior border, replaces the deflector $M_3$ of the embodiment of FIGS. 6-7. The cross-sectional projection 142 of the curve of the mirror 140 may correspond to the desired post-operative shape of the altered cornea. In the embodiment of FIG. 14, element 140, which may be one of a series of specially configured mirrors, deflects laser beam 141 into a fat, finitely-thick curved-profile beam 143 to effect the above-described tangential corneal ablation resulting in a particular curve shaped cornea. In some embodiments, a wide variety of such curved elements 140 may be provided in a "kit" such that a particular element may be chosen to fit a particular corneal profile. The curved profile of element 140 avoids the need to provide rotation of the aiming element in the direction of arrow 77 in FIG. 6 while maintaining the curved pattern of the striking laser beam. Translation of curved element 140 in the direction of arrow 146 (FIG. 14) may be provided using a mechanism similar to that described for providing translation of element $M_3$ in FIGS. 6-7.

Figure 16:
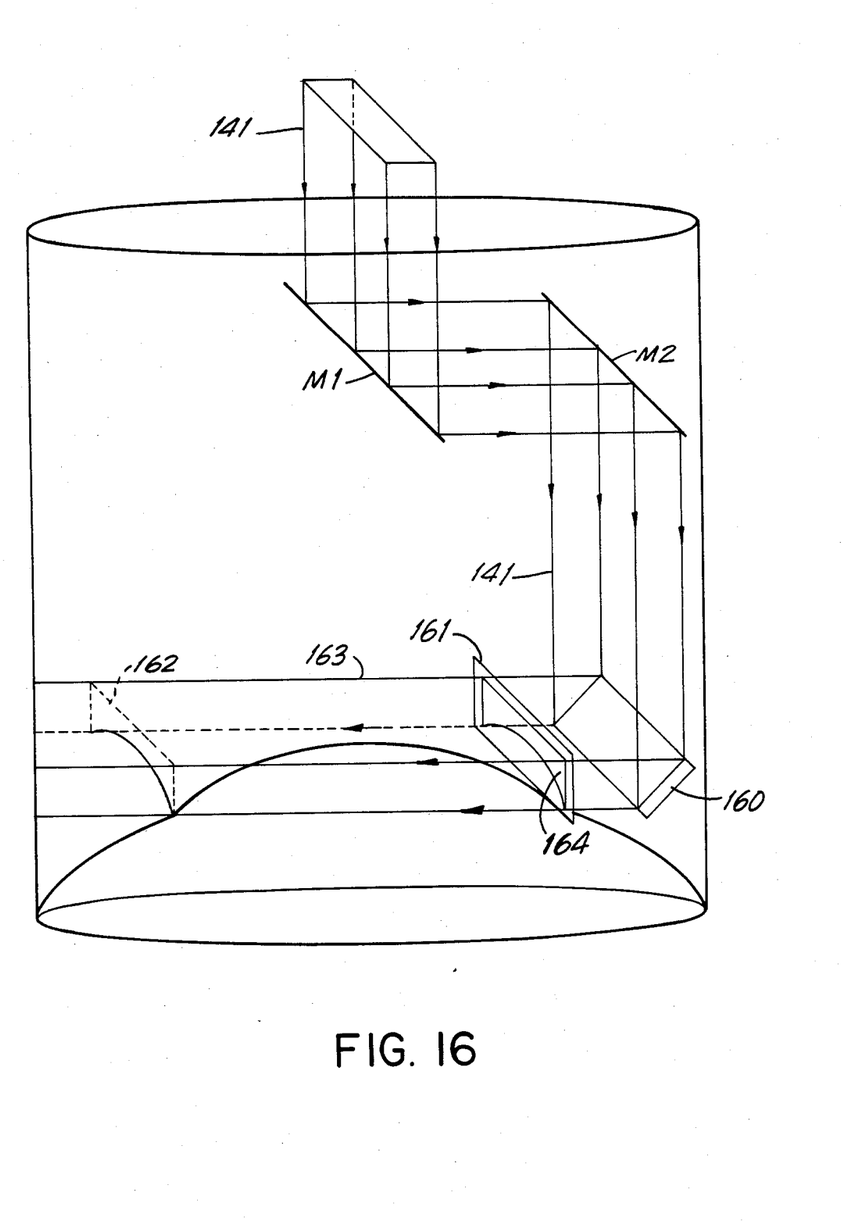
FIG. 16 is a partial perspective view of a further embodiment providing a contoured laser beam.

FIG. 16 similarly illustrates an embodiment of the invention wherein a curved profile laser beam is provided to effect corneal ablation. In the embodiment of FIG. 16, the laser beam 163 deflected by a rectangular mirror 160 passes through a mask 161 having a curved opening 164 provided therein. The resultant contoured laser beam 163 has a cross-sectional profile 162 which matches the desired post-operative corneal contour. A variety of masks may be provided in "kit" form to match a variety of desired corneal profiles.

Figure 15:
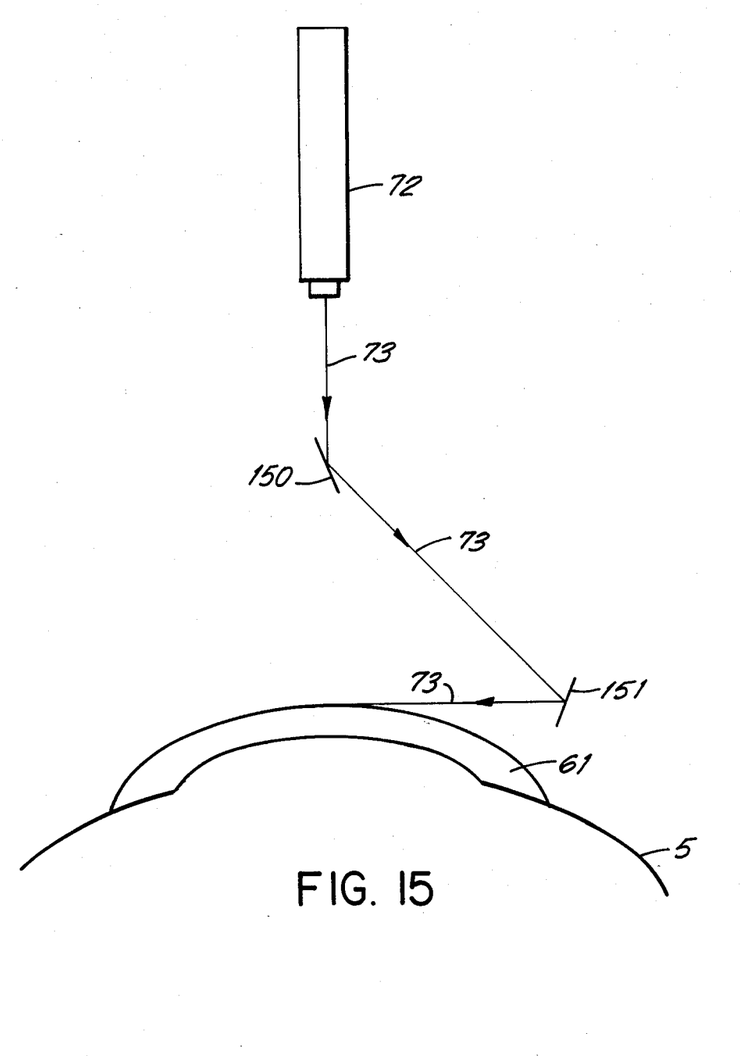
FIG. 15 is a schematical view of a further embodiment of the invention.

FIG. 15 illustrates a further emodiment of the invention using only two rotating deflective members 150, 151 to direct the laser beam to strike the cornea 61 tangentially. In this embodiment, light from the laser source strikes incident element 150 which deflects the beam to element 151. The geometric relationship between the first element 150 and the second element 151 eliminates the need for the intermediate element $M_2$ of the embodiment of FIGS. 6-7. Alternatively, the curved optical element 140 of FIG. 14, or the masked element 160, 161 of FIG. 15, may be provided as the second deflector in this two-element embodiment.

Since the laser beam in an apparatus according to the invention is preferably maintained consistently tangential to the corneal surface, only the portion of the cornea that actually touches the beam is subject to ablation. Studies have indicated that precise control of corneal cutting by an ultraviolet laser can yield negligible effects on corneal tissue immediately adjacent to the beam, yielding extremely precise effects. Particularly preferred are ultraviolet lasers such as the excimer type of far-ultraviolet laser. One example is a Model 201E excimer laser from Lambda Physik, Gottingen, West Germany. Such lasers, charged with argon-fluoride gas, have been shown to be precise at wavelengths of 193 nm. The laser output of such a laser may be pulsed with typical pulse energies of more than 300 mJ at a repetition rate of as much as 400 pulses per second. Alternatively, radiation from a frequency doubled or quadrupled Nd:YAG laser (Quanta-Ray DCR) may be employed giving frequencies in the ultraviolet range.

Figure 13:
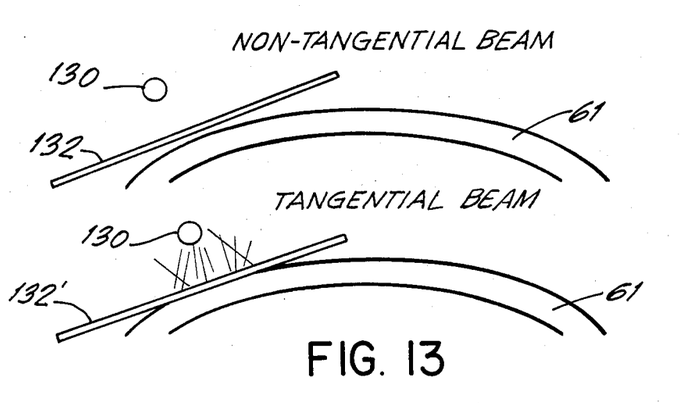
FIG. 13 illustrates the functioning of a light scatter detector used to determine tangentiality in one apparatus according to the invention.

As the light emitted from a laser is coherent, tangentiality can be monitored utilizing perpendicular light scattering techniques for detecting when a laser beam intersects the surface of the cornea tangentially. FIG. 13 illustrates the function of such a light scatter detector 130 which may be provided in an apparatus according to the invention so as to be in close proximity to the cornea 61 during operation of the invention. A first output signal may be provided by the light scatter detector 130 when a laser beam 132 is in a non-tangential pattern relative to the cornea 61 and a second output signal may be provided to the computer when the laser beam 132 intercepts the cornea tangentially.

Preferably, the laser source 72 (FIG. 7) of the invention will be a non-thermal laser such as an ultraviolet or excimer laser as described above. However, thermal or infra-red lasers can also be used. The ultraviolet lasers are currently preferred as they provide precise beams of energy which break apart protein bonds, ablating or vaporizing the cornea as opposed to burning the cornea as caused by thermal lasers. Of course, a wide variety of laser or other radiation sources may be provided within the spirit and scope of the invention.

Figure 9:
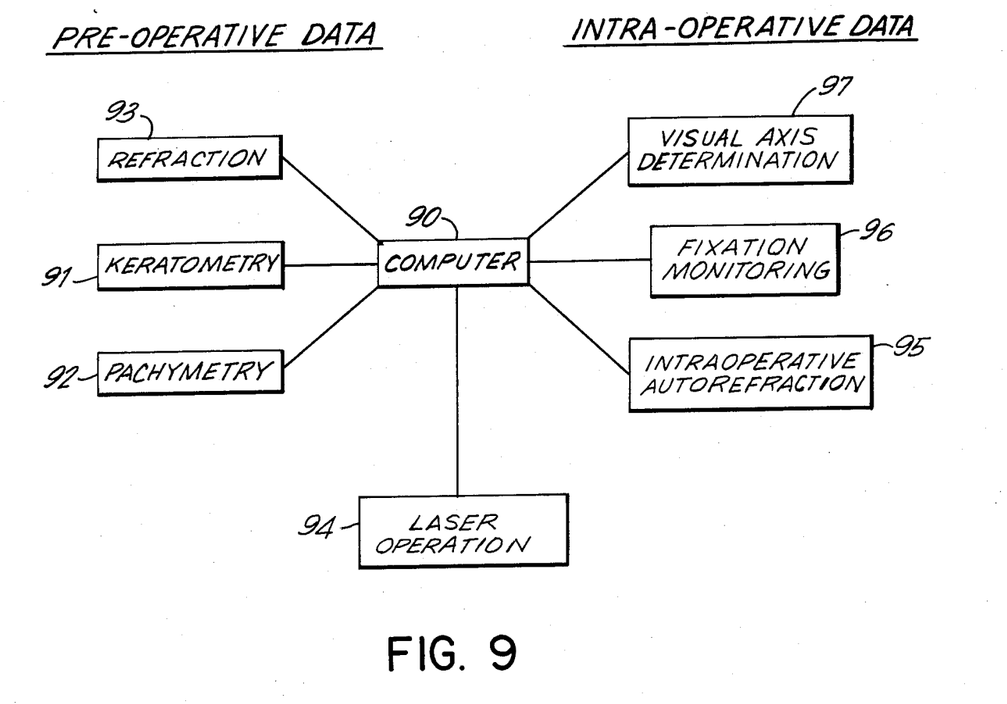
FIG. 9 is a control chart illustrating the functions of a command computer in an apparatus according to the invention.

FIG. 9 illustrates the high degree of computer coordination which can be provided in an apparatus according to the invention. For example, pre-operatively, data can be fed into the system computer 90 to determine whether an operation according to the invention is viable. Such data can include pre-operative refraction data 93 to determine how much refractive error needs to be corrected, keratometric data 91 in terms of the diopters of corneal refractive power, and pachymetric data 92 or the measurements of the pre-operative corneal thickness. Using known calculation techniques, the computer can determine whether the procedure will be viable and accordingly signal the operator.

Intra-operatively, the computer 90 may also be used to monitor intraoperative data to insure that the system is operating safely and effectively. For example, the computer 90 can monitor the visual axis determination 97, fixation 96, as well as intra-operative autorefraction 95. Individual apparatuses for determining these individual conditions are generally known.

Additionally, the computer 90 operates the laser including signalling of the laser 72 (FIG. 6) to emit the laser beam 73, controlling the frequency and speed of rotation of the arm 70 and controlling the rotation and translation of variable mirror M$_3$ or the translation of element 140 (FIG. 14). It should be understood that the degree of lathing and the length of the lathing procedure will depend on various factors, including the strength and the diameter of the laser beam, the speed of arm rotation and the number of arm rotations required. Thus, accurate computer assistance will preferably be provided in an apparatus according to the invention to coordinate the many variables and provide the various calculations.

FIG. 11 illustrates the operation of an apparatus according to the invention. First, pre-operative refraction data is provided to the system computer to establish whether hyperopia or myopia is present and to determine how much refractive error to correct. Keratometry and pachymetry data are then provided to the computer to determine whether the patient has enough corneal tissue to safely carry out the lathing procedure. If not enough corneal tissue is available to safely carry out the procedure, then the operator will be so notified and the laser procedure will be disabled. Depending upon the pre-operative data, beginning positions of the variable mirror will be established. If sufficient corneal tissue is present, the computer may then be set to check that fixation has been maintained. If fixation has not been maintained, the laser will be disabled. If fixation is present, the laser will be activated. Note that at any time fixation is lost, the computer will automatically disable the laser. While the laser is activated, the tangent monitor will be constantly operating to determine whether the laser is tangential to the cornea. If the laser is not tangential to the cornea, the variable element will be adjusted until tangentiality is achieved. Tangentiality may be constantly monitored through either system interrupts or polling procedures. Assuming tangentiality is achieved, and the laser lathing process is under way, the system autorefractor will constantly monitor the intra-operative refractive state of the patient until either emmetropia or a pre-set condition has been reached. At this point, the laser will be deactivated.

The invention thus provides a method and apparatus for reshaping the cornea of the patent in vivo without the need for removing, reshaping and then suturing the modified corneal tissue back in place. In addition, with the invention, there is no need for freezing the corneal tissue prior to reshaping it, although the technique could easily be used with corneal tissue in the frozen state in conjunction with known lamellar keratoplasty techniques.

In the invention, radiant energy, from either a non-thermal laser such as an ultraviolet or "excimer" laser or a thermal laser such an infra-red laser can be used to modify the corneal curvature, and thereby its refractive properties, in vivo or in vitro to shave away or vaporize part of the optical zone of the cornea in a precisely calibrated and predictable manner. The invention obviates the need for blades for cutting or mechanical lathing and also obviates the need for suturing or unpredicably scarring the cornea of the patient as was required in various prior known methods. Additionally, since the incident laser beam touches the cornea only tagentially, rather than perpendicularly, changes in the lasers power output would not carry the risk of perforation of the cornea, as there would be no additional tissue in the path of the beam to be further exposed to damaging irradiation. Thus, the delicate intraoccular structures would not be directly exposed to the effects of the laser. The invention thus provides a safe, effective and reproducible method and apparatus for modifying corneal refractive properties.

Although the invention has been described in great detail above by way of reference to the accompanying drawings, it should be understood that a wide variety of embodiments may be provided within the spirit and scope of the invention and that the invention should not be limited to the specific embodiments herein disclosed, but should be interpreted only in accordance with the claims which follow.

I claim:

1. An apparatus for modifying the refractive properties of the cornea of an eye, comprising:

laser means for emitting a laser beam;

means for deflectng said laser beam to strike said cornea tangentially about the optical zone thereof; and means for rotating said deflecting means through 360°, the center of rotation of said deflecting means being positioned substantially along the visual axis of said cornea, such that through rotation of said deflecting means, said laser beam strikes said cornea tangentially over an area substantially centered about the visual axis of said cornea.

2. An apparatus according to claim 1, further comprising: means for determining whether said visual axis is aligned with said center of rotation and control means for disabling said laser means when said visual axis and said center of rotation are not aligned.

3. An apparatus according to claim 1, further comprising; autorefraction means for determining the refractive properties of an eye; and control means for disabling said laser means when said refractive properties meet predetermined conditions.

4. An apparatus according to claim 1, further comprising: tangentiality detecting means for detecting tangential striking of the cornea by said laser beam; adjusting means for adjusting said deflecting means to alter the angle and point at which said laser beam strikes said cornea; and control means for effecting adjustment by said adjusting means until tangentiality is indicated by said tangentiality indicating means.

5. The apparatus according to claim 1, wherein said deflecting means includes means for contouring a laser beam to have a curved cross-sectional profile.

6. The apparatus according to claim 5, wherein said deflecting means includes a curved deflector.

7. The apparatus according to claim 5, wherein said deflecting means includes masking means defining a curved profile.

8. An apparatus for modifying the refractive properties of the cornea of an eye, comprising:

laser means for emitting a laser beam along an incidental axis;

rotating deflection means, having its center of rotation disposed substantially along said incidental axis, comprising first deflecting means disposed along said incidental axis for deflecting said laser beam radially outward, second deflecting means displaced substantially perpendicularly from said incidental axis and aligned with said first deflecting means for deflecting said laser beam from said first deflecting means to a third deflecting means aligned with said second deflecting means in a line substantially parallel to sid incidental axis;

means for maintaining alignment between the visual axis of an eye and said incidental axis; and means for adjusting said third deflecting means such that said laser beam deflected thereby is adapted to strike the surface of a cornea tangentially, rotation of said rotating deflection means about said incidental axis causing said laser to strike the cornea tangentially over an area substantially centered about the visual axis of said cornea.

9. An apparatus as recited in claim 8, wherein the cross-sectional projection of a laser beam deflected by said third deflecting means substantially corresponds to post-operative corneal curvature.

10. A method for in vivo modification of the refractive properties of a patient's eye, comprising the steps of:
   (a) maintaining visual fixation;
   (b) ascertaining the visual axis of the eye;
   (c) activating laser means to emit a laser beam;
   (d) directing said laser beam through deflecting means to strike the cornea of the eye tangentially about the optical zone thereof; and
   (e) rotating said deflecting means through 360° substantally about said visual axis while maintaining tangential striking of the cornea by the laser beam.

11. A method according to claim 10, further comprising the steps of:
   (f) ascertaining the refractive error of the eye; and
   (g) if refractive error is found, repeating the step of (a)–(f).

12. The method of claim 10 further comprising the step of translating said laser beam across said cornea, the rotation and translation of said laser beam resulting in a spiraling pattern of corneal ablation.

13. An apparatus for modifying the refractive properties of the cornea of an eye, comprising:
   laser means for emitting a laser beam;
   means for deflecting said laser beam to strike said cornea tangentially;
   means for rotating said deflecting means through 360°, the center of rotation of said deflecting means being positioned along the visual axis of said cornea, such that through rotation of said deflecting means, said laser beam strikes said cornea tangentially over an area centered about the visual axis of said cornea; and
   means for determining whether said visual axis is aligned with said center of rotation and control means for disabling said laser means when said visual axis and said center of rotation are not aligned.

14. The apparatus according to claim 13, further comprising means for contouring said laser beam to have a curved cross-sectional profile.

15. An apparatus for modifying the refractive properties of the cornea of an eye, comprising:
   laser means for emitting a laser beam;
   means for deflecting said laser beam for strike said cornea tangentially;
   means for rotating said deflecting means through 360°, the center of rotation of said deflecting means being positioned substantially along the visual axis of said cornea, such that through rotation of said deflecting means, said laser beam strikes said cornea tangentially over an area centered about the visual axis of said cornea; and
   tangentiality detecting means for detecting tangential striking of the cornea by said laser beam; adjusting means for adjusting said deflecting means to alter the angle and point at which said laser beam touches the cornea; and control means for effecting adjustment by said adjusting means until tangentiality is indicated by said tangentiality indicating means.

16. The apparatus according to claim 15, further comprising means for contouring said laser beam to have a curved cross-sectional profile.

17. A method for in vivo modification of the refractive properties of a patient's eye, comprising the steps of:
   (a) maintaining visual fixation;
   (b) ascertaining the visual axis of the eye;
   (c) activating laser means to emit a laser beam;
   (d) directing said laser beam through deflecting means to strike the cornea of the eye tangentially;
   (e) rotating said deflecting means through 360° substantially about said visual axis while maintaining tangential striking of the cornea by the laser beam;
   (f) ascertaining the refractive error of the eye; and
   (g) if refractive error is found, repeating the steps of (a)–(f).

18. The method of claim 9, further comprising the step of contouring said laser beam to have a curved cross-sectional profile.

19. A method for modification of the refractive properties of a cornea, comprising the steps of:
   (a) activating laser means to emit a laser beam;
   (b) directing said laser beam to strike the cornea tangentially about the optical zone thereof; and
   (c) rotating said laser beam through 360° while substantially maintaining tangential striking of the cornea by the laser beam.

20. A method according to claim 19, the rotation of said laser beam being centered substantially about the visual axis of said cornea.

21. The method according to claim 20, further comprising the step of contouring said laser beam to have a curved cross-sectional profile.

22. The method according to claim 19, further comprising the step of contouring said laser beam to have a curved cross-sectional profile.

23. The method of claim 19 further comprising the step of translating said laser beam across said cornea, the rotation and translation of said laser beam resulting in a spiraling pattern of corneal ablation.

24. The method of claim 19 wherein the method is performed in vivo.

25. The method of claim 19 wherein the method is performed in vitro.

26. An apparatus for modifying the refractive properties of the cornea of an eye, comprising:
   laser means for emitting a laser beam along an incidental axis;
   rotating deflection means, having its center of rotation disposed along said incidental axis, comprising first deflecting means disposed along said incidental axis for deflecting said laser beam outward and second deflecting means displaced a distance from said incidental axis and adapted to deflect said laser beam towards the cornea; and
   means for adjusting said first and second deflecting means such that said laser beam deflected thereby is adapted to strike the surface of the cornea tangentially about the optical zone thereof, rotation of said rotating deflection means about said incedental axis causing said laser to strike the cornea tangentially over an area substantially centered about the visual axis of said cornea.

27. An apparatus as recited in claim 26, wherein the cross-sectional projection of a laser beam deflected by said second deflecting means substantially corresponds to pre-determined post-operative corneal curvature.

28. An apparatus as recited in claim 26, further comprising means for contouring said laser beam to have a curved cross-sectional profile.

29. An apparatus for modifying the refractive properties of a cornea, comprising:
laser means for emitting a laser beam;
means for directing said laser beam to strike said cornea tangentially about the optical zone thereof; and
means for rotating said laser beam through 360°, the center of rotation of said laser beam being substantially along the visual axis of said cornea, such that through rotation of said laser beam, said laser beam strikes said cornea tangentially over an area centered substantially about the visual axis of said cornea.

30. An apparatus according to claim 29, further comprising: means for determining whether said visual axis is substantially aligned with said center of rotation and control means for disabling said laser means when said visual axis and said center of rotation are not substantially aligned.

31. An apparatus according to claim 29, further comprising: autorefraction means for determining the refractive properties of the cornea; and control means for disabling said laser means when said refractive properties meet predetermined conditions.

32. An apparatus according to claim 29, further comprising: tangentiality detecting means for detecting tangential striking of the cornea by said laser beam; adjusting means for adjusting said deflecting means to alter the angle and point at which said laser beam touches the cornea; and control means for effecting adjustment by said adjusting means until tangentiality is indicated by said tangentiality indicating means.

33. The apparatus according to claim 29, further comprising means for contouring said laser beam to have a curved cross-sectional profile.

34. The apparatus according to claim 33, wherein said means for contouring includes a curved deflector.

35. The apparatus according to claim 33, wherein said means for contouring includes masking means defining a curved profile.

36. An apparatus according to claim 29, further comprising means for detecting fixation of an operative eye directly from said operative eye.

37. An apparatus for modifying the refractive properties of a cornea, comprising:
laser means for emitting a laser beam;
means for directing said laser beam to strike said cornea tangentially about the optical zone thereof; and
means for rotating said laser beam through 360°, such that through rotation of said laser beam, said laser beam strikes said cornea tangentially over an area substantially centered about the visual axis of said cornea.

38. An apparatus according to claim 37, wherein rotation of said laser beam is centered substantially about the visual axis of said cornea, said apparatus further comprising means for determining whether said visual axis is substantially aligned with said center of rotation and control means for disabling said laser means when said visual axis and said center of rotation are not substantially aligned.

39. An apparatus according to claim 37, further comprising: autorefraction means for determining the refractive properties of the cornea; and control means for disabling said laser means when said refractive properties meet predetermined conditions.

40. An apparatus according to claim 37, further comprising: tangentiality detecting means for detecting tangential striking of the cornea by said laser beam; adjusting means for adjusting said deflecting means to alter the angle and point at which said laser beam touches the cornea; and control means for effecting adjustment by said adjusting means until tangentiality is indicated by said tangentiality indicating means.

41. The apparatus according to claim 37, further comprising means for contouring said laser beam to have a curved cross-sectional profile.

42. A method for modification of the refractive properties of a cornea, comprising the steps of:
(a) activating high intensity radiation means to emit a beam;
(b) directing said beam to strike the cornea tangentially about the optical zone thereof; and
(c) rotating said beam through 360° while substantially maintaining tangential striking of the cornea by the beam.

43. A method according to claim 42, the rotation of said beam being centered substantially about the visual axis of said cornea.

44. The method according to claim 43, further comprising the step of contouring said beam to have a curved cross-sectional profile.

45. The method according to claim 42, further comprising the step contouring said beam to have a curved cross-sectional profile.

46. An apparatus for modifying the refractive properties of a cornea, comprising:
high intensity radiation means for emitting a beam;
means for directing said beam to strike said cornea tangentially about the optical zone thereof; and
means for rotating said beam through 360°, such that through rotation of said beam, said beam strikes said cornea tangentially over an area substantially centered about the visual axis of said cornea.

47. An apparatus according to claim 46, wherein rotation of said beam is centered substantailly about the visual axis of said cornea, said apparatus further comprising means for determining whether said visual axis is substantially aligned with said center of rotation and control means for disabling said high intensity radiation means when said visual axis and said center of rotation are not substantially aligned.

48. An apparatus according to claim 46, further comprising: autorefraction means for determining the refractive properties of the cornea; and control means for disabling said high intensity radiation means when said refractive properties meet predetermined conditions.

49. An apparatus according to claim 46, further comprising: tangentiality detecting means for detecting tangential striking of the cornea by said beam; adjusting means for adjusting said deflecting means to alter the angle and point at which said beam touches the cornea; and control means for effecting adjustment by said adjusting means until tangentiality is indicated by said tangentiality indicating means.

50. An apparatus according to claim 46, further comprising means for contouring said beam to have a curved cross-sectional profile.

* * * * *